(12) United States Patent
Santarelli et al.

(10) Patent No.: US 9,440,965 B2
(45) Date of Patent: Sep. 13, 2016

(54) PROCESS FOR THE SYNTHESIS OF BENZOTHIADIAZOLE COMPOUNDS

(75) Inventors: Samuele Santarelli, Novara (IT); Marco Ricci, Novara (IT); Roberto Fusco, Novara (IT)

(73) Assignee: ENI S.P.A. (IT)

( * ) Notice: Subject to any disclaimer, the term of this patent is extended or adjusted under 35 U.S.C. 154(b) by 613 days.

(21) Appl. No.: 13/809,646

(22) PCT Filed: Jul. 13, 2011

(86) PCT No.: PCT/IB2011/001650
§ 371 (c)(1),
(2), (4) Date: Jun. 18, 2013

(87) PCT Pub. No.: WO2012/007834
PCT Pub. Date: Jan. 19, 2012

(65) Prior Publication Data
US 2015/0291575 A1    Oct. 15, 2015

(30) Foreign Application Priority Data
Jul. 16, 2010  (IT) ............................. MI2010A1316

(51) Int. Cl.
*C07D 285/14*  (2006.01)
*C07D 417/14*  (2006.01)

(52) U.S. Cl.
CPC ........... *C07D 417/14* (2013.01); *C07D 285/14* (2013.01)

(58) Field of Classification Search
CPC .......................... C07D 285/06; C07D 285/14
See application file for complete search history.

(56) References Cited

PUBLICATIONS

Fei, 2011, Science China Press, vol. 54, No. 4, p. 617-624.*
Liang, 2010, vol. 94, o. 1803-1808.*
Yoo, J. Am. Chem. Soc. 2006, vol. 128, p. 16384-16393.*
Meijer, E.W., et al., "Band-Gap engineering of donor-acceptor-substituted PI-conjugated polymers", Chemistry—A European Journal, vol. 4, No. 7, Jan. 1, 1998.

* cited by examiner

*Primary Examiner* — Rebecca Anderson
*Assistant Examiner* — Karen Cheng
(74) *Attorney, Agent, or Firm* — Tarolli, Sundheim, Covell & Tummino LLP

(57) ABSTRACT

The invention relates to a significantly improved process for the preparation of benzothiadxazole compounds which can be used in the production of Luminescent Solar Concentrators, (LSC). In particular, the synthesis process of the present invention is oriented towards the preparation of 4,-di-2-thienyl-2,1,3-benzo-thiadiazole.

14 Claims, No Drawings

PROCESS FOR THE SYNTHESIS OF BENZOTHIADIAZOLE COMPOUNDS

This application is a National Phase filing of PCT/IB2011/001650, filed Jul. 13, 2011, the subject matter which is incorporated herein by reference in its entirety, which claims priority from Italian Application No. MI2010A001316, filed Jul. 16, 2010.

The invention relates to a significantly improved process for the preparation of benzothiadiazole compounds which can be used in the production of Luminescent Solar Concentrators, (LSC).

The synthesis process of the present invention is preferably oriented towards the preparation of 4,7-di-2-thienyl-2,1,3-benzothiadiazole. It is known that photovoltaic cells, including silicon photovoltaic cells which are currently the most widespread on the market, are not capable of effectively exploiting all solar radiation. Their efficiency is maximum only within a limited spectral range which comprises a part of visible radiation and a part of infrared radiation.

In order to improve the performance of the cells, spectrum converter materials can be used, which capture the solar radiation outside the optimum spectral range, and convert it into effective radiation. With these materials, it is also possible to produce luminescent solar concentrators which allow a further increase in the production of current by the cells.

These concentrators consist of large sheets of material transparent to solar radiation, in which fluorescent substances are dispersed, which act as spectrum convertors. Due to the total reflection optical phenomenon, the radiation emitted by the fluorescent molecules is "guided" towards the thin edges of the sheet where it is concentrated on solar cells placed therein. In this way, large surfaces of low-cost materials can be used (photoluminescent sheets) to concentrate the light on small surfaces of high-cost materials (solar cells).

It is known that some benzothiadiazole materials and, in particular, 4,7-di-2-thienyl-2,1,3-benzothia-diazole (DTB), are, in fact, fluorescent substances which can be used as spectrum convertor materials and in luminescent solar concentrators. Materials of this type are described, for example, in Italian Patent Application MI2009A 001796.

DTB is a compound of great interest, whose synthesis has been the object of numerous research studies. It is normally prepared by means of a reaction of 4,7-dibromo-2,1,3-benzothiadiazole and an excess of tri-n-butyl-(thien-2-yl)stannane, two products which are easily available on the market.

The reaction is normally carried out in the presence of palladium-based catalysts, at temperatures ranging from 60 to 120° C., in solvents such as toluene, xylenes, 1,2-dimethoxyethane and, most often, tetrahydrofuran (THF). Under these conditions, the reaction lasts from 3 to 18 hours. The yields normally range from 70 to 88%. According to what is described in *Chem. Mater.*, 1996, 8, 570-578, for example, DTB can be prepared starting from 4,7-dibromo-2,1,3-benzothiadiazole and tri-n-butyl-(thien-2-yl)stannane (2.4 equivalents, i.e. an excess of 20%) in THF at reflux temperature (about 66° C.) in 3 hours. Palladium chloride bistriphenylphosphine $(PPh_3)_2PdCl_2$ is used as catalyst (2 moles per 100 moles of 4,7-dibromo-2,1,3-benzothiadiazole). At the end of the reaction, the solvent is removed by evaporation at reduced pressure and the residue is purified by silica gel column chromatography, using a 1:1 mixture of n-hexane and dichloromethane as eluent. The fractions containing DTB are collected, the solvent is removed at reduced pressure and the residue is crystallized from a mixture of ethanol and toluene obtaining pure DTB with 82% yield.

An analogous preparation is described in *J. Mater. Chem.*, 2008, 18, 5223-5229. Also in this case, at the end of the test, the reaction raw product must be eluted on a chromatographic column (silica gel, eluent n-hexane/dichloromethane 1:1) and the product then crystallized form ethanol, instead of the toluene/ethanol mixture. Pure DTB is obtained with a yield of 88%.

The reaction can also be catalyzed from complexes of palladium in oxidation state (0), instead of (II) as described above. In WO 2001/49768, the reaction between 4,7-dibromo-2,1,3-benzothiadiazole and tri-n-butyl-(thien-2-yl)stannane (also in this case used with an excess of 20%) is carried out in toluene at reflux temperature (about 110° C.) for 18 hours, in the presence of tetrakis(triphenylphosphine)palladium(0), again in an amount of 2 moles per 100 moles of 4,7-dibromo-2,1,3-benzothiadiazole. At the end, the reaction mixture is cooled to room temperature and filtered on celite. The solvent is removed from the filtrate by evaporation at reduced pressure and the residue washed with hexane obtaining pure DTB with a yield of 95%.

Although the known preparations of DTB allow the desired product to be obtained with good yields and a high purity, they still have several disadvantages. In particular:

although the yields are high, they normally range from 70 to 88% so that, at the end of the reaction, the DTB must generally be purified by column chromatography which prohibits any scale-up of the procedure; WO 2001/49768 describes a yield of 95%, which, however, in order to recover the DTB with suitable purity, requires a filtration on celite and a subsequent washing with hexane;
 to be completed, the reactions require relatively long times, ranging from a few hours to a few tens of hours (normally from 3 to 72 hours) and an excess of tri-n-butyl-(thien-2-yl)stannane, with consequent higher production costs and increased costs for the disposal of the waste-products;
 the amounts of catalyst are relatively high: 2 moles of palladium per 100 moles of 4,7-dibromo-2,1,3-benzothiadiazole are normally used and in any case never less than 0.5 moles per 100 moles of dibromo-derivative. Although these amounts are small in absolute, they are significant considering the cost of palladium or (as it is not always possible to prepare its complexes in situ) its complexes;
 some of the proposed solvents creates problems of toxicity and high disposal costs.

A process has now been surprisingly found for preparing benzothiadiazole compounds, which can be used as spectrum convertor materials and as materials which are adopted in the production of luminescent solar concentrators, which uses particular solvents and reaction conditions and allows a high reaction rate to be obtained, with a reduction in the amount of catalyst, with short reaction times and operating in stoichiometric ratios.

In particular, the process of the present invention uses a solvent selected from dimethylsulfoxide (DMSO) and dimethylformamide (DMF) and is run at temperatures higher than 110° C., even more preferably at temperatures higher than 120° C.

The object of the present invention therefore relates to a process for the preparation of compounds having general formula (A)

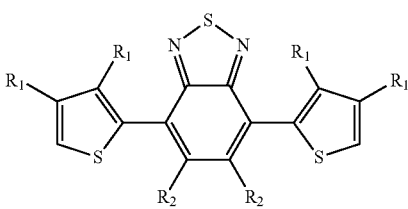

wherein:
the two thienyl groups —$C_4HS(R_1)_2$ are the same,
each $R_1$ of the thienyl group is independently selected from H, linear or branched alkyl, cycloalkyl, aryl, alkyl-aryl, alkoxyl, substituted alkoxyl,
each $R_2$ is independently selected from H, linear or branched alkyl, cycloalkyl, aryl, alkyl-aryl, alkoxyl, substituted alkoxyl, or
the adjacent $R_1$ groups of the thienyl group and/or adjacent $R_2$ groups, are bound to each other and, together with the carbon atoms to which they are bound, form a cycle or a polycyclic system, aliphatic or aromatic, possibly containing one or more heteroatoms,
wherein said process comprises reacting, in the presence of a catalyst containing Pd, at a temperature higher than 110° C. and in the presence of a solvent selected from dimethylsulfoxide (DMSO) and dimethylformamide (DMF), a compound having formula (B),
wherein:
X is a halogen selected from Cl, Br and I,
each $R_2$ is independently selected from H, linear or branched alkyl, cycloalkyl, aryl, alkyl-aryl, alkoxyl, substituted alkoxyl, or the adjacent $R_2$ groups are bound to each other and, together with the carbon atoms to which they are bound, form a cycle or a polycyclic system, aliphatic or aromatic, possibly containing one or more heteroatoms,

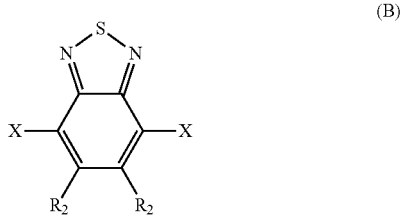

(B)

with a compound having formula (C)

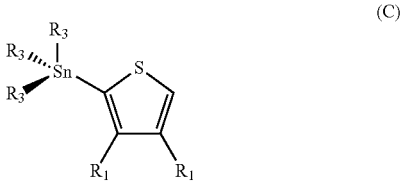

(C)

wherein:
each $R_1$ is independently H, linear or branched alkyl, cycloalkyl, aryl, alkyl-aryl, alkoxyl, substituted alkoxyl, or the $R_1$ adjacent groups are bound to each other and, together with the carbon atoms to which they are bound, form a cycle or a polycyclic system, aliphatic or aromatic, possibly containing one or more heteroatoms, and $R_3$ is an alkyl containing from 1 to 6 carbon atoms.

When at least one of the $R_1$ groups and/or at least one of the $R_2$ groups is linear or branched alkyl, cycloalkyl, aryl, alkyl-aryl, alkoxyl, alkoxyl-substituted, said group preferably contains from 1 to 10 carbon atoms, even more preferably from 1 to 6 carbon atoms. A particularly preferred aspect is for all the $R_1$ and $R_2$ groups to be H.

When the adjacent $R_1$ groups and/or the adjacent $R_2$ groups are bound to each other, together with the carbon atoms to which they are bound, they form a cycle or a polycyclic system, possibly containing one or more aliphatic or aromatic heteroatoms, preferably containing from 3 to 14 carbon atoms, and even more preferably from 4 to 6 carbon atoms. In the case of heterocycles, the heteroatoms present can, for example, be nitrogen, oxygen or sulfur. In particular, the adjacent $R_1$ groups and/or adjacent $R_2$ groups can be bound to each other and form a —$OCH_2CH_2O$— unit. $R_3$ is preferably an alkyl containing from 1 to 4 carbon atoms.

Operating according to the process of the present invention, the reaction rate is extremely high and at the same time, with respect to the known processes, it is possible to:
reduce the amount of palladium contained in the catalyst by up to 40 times, also using easily preparable complexes in situ;
complete the reaction in shorter times, preferably less than an hour, even more preferably ranging from 10 to 35 minutes;
use stannane having formula (C) in a stoichiometric amount, obtaining practically complete conversions of both the reagents with yields in the order of 98-100%, sufficiently high as to not require complex purifications.

It should also be noted that both DMSO and DMF are solvents which can be easily re-used or disposed of. DMSO in particular is by far the least toxic among dipolar aprotic solvents, so much so that it can be also be used in medicine.

All of these factors also contribute to ensuring that the process of the invention has a significant advantage from the point of view of production and waste-disposal costs, much lower than those of the preparations described so far in literature.

A preferred aspect of the present invention is a process for preparing 4,7-di-2-thienyl-2,1,3-benzo-thiadiazole (DTB), having the following formula (I), corresponding to a compound having formula (A) wherein all the $R_1$ and $R_2$ groups are H, by reaction of 4,7-di-halogen-2,1,3-benzothiadiazole, corresponding to a compound having formula (B) wherein X is a halogen selected from Cl, Br and I, and the $R_2$ groups are H, with tri-alkyl-(thien-2-yl)stannane, corresponding to a compound having formula (C), wherein the $R_1$ groups are hydrogen and $R_3$ is alkyl containing from 1 to 6 carbon atoms, said process being carried out in the presence of a catalyst containing Pd, at a temperature higher than 110° C. and in the presence of a solvent selected from dimethylsulfoxide (DMSO) and dimethylformamide (DMF).

A particularly preferred aspect of the present invention relates to a process for preparing 4,7-di-2-thienyl-2,1,3-benzothiadiazole (DTB), having formula (I), corresponding to a compound having formula (A) wherein all the $R_1$ and $R_2$ groups are H, by reaction of 4,7-di-bromo-2,1,3-benzothiadiazole, having formula (II), corresponding to a compound having formula (B) wherein X is Br and the $R_2$ groups are H, with tri-n-butyl-(thien-2-yl)stannane, having formula (III), corresponding to a compound having formula (C), wherein the $R_1$ groups are hydrogen and $R_3$ is n-butyl, wherein said process is carried out in the presence of a catalyst containing Pd, at a temperature higher than 110° C. and in the presence of a solvent selected from dimethylsulfoxide (DMSO) and dimethylformamide (DMF).

The reaction is the following:

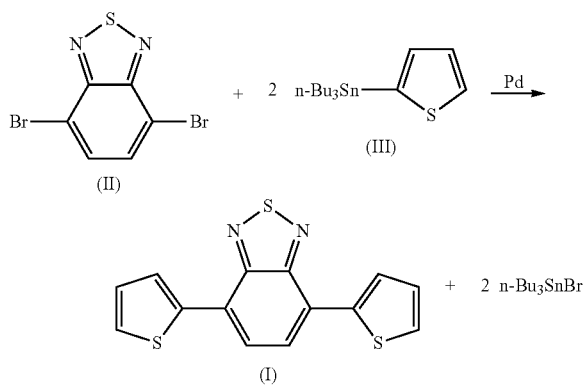

The compounds having formula (B) are prepared by means of the known techniques, for example by halogenation of the corresponding 2,1,3-benzothiadiazoles. In WO 2007/081991, Example 60, the introduction of iodine is described, for the preparation of 4,7-diiodo-2,1,3-benzothiadiazole; when, in particular, the compound having formula (B) is 4,7-dibromo-2,1,3-benzothiadiazole (II), i.e. a compound having formula (B) wherein X is bromine and the $R_2$ groups are H, said compound can be prepared by bromination of 2,1,3-benzothiadiazole with hydrobromic acid as described, for example in K. Pilgram et al., *J. Heterocycl. Chem.*, 1970, 7, 629.

The compounds having formula (C) are prepared from the corresponding thiophene, for example by reaction with n-butyllithium or with lithium di-iso-propylamide (LDA) and with the corresponding trialkyl stannyl chlorides, as described, for example, in E. Bundgaard et al., *Macromolecules* 2006, 39, 2823.

In particular, when the compound having formula (C) is tri-n-butyl-(thien-2-yl)stannane (II), i.e. a compound having formula (C) wherein the $R_1$ groups are H, and $R_3$ is n-butyl, said compound can be prepared as described in J. T. Pinhey et al., *J. Chem. Soc. Perkin Trans.* 1, 1988, 2415. The reaction stoichiometry requires that the molar ratio between the stannane having formula (C) and benzothiadiazole having formula (B) be equal to 2. In the known art, in order to complete the reaction, the use of higher ratios is commonly described and in most cases reference is made to a 2.4 ratio. The process of the present invention does not require this excess, it can be conveniently effected with ratios higher than or equal to 2, and, according to a preferred aspect a ratio equal to 2 is adopted.

The process of the present invention is catalyzed by palladium complexes. The oxidation state of the palladium can be (0) or, preferably, (II). Complexes which can be used for catalyzing the reaction are, for example, the following complexes, of which the formula is indicated in square brackets:

bis(triphenylphosphine)palladium(II) chloride [Pd(PPh$_3$)$_2$Cl$_2$]
bis(triphenylphosphine)palladium (II) acetate [Pd(PPh$_3$)$_2$(OAc)$_2$],
tetrakis(triphenylphosphine)palladium (0) [Pd(PPh$_3$)$_4$],
bis(dibenzylideneacetone)palladium (0) [Pd(dba)$_2$; dba: C$_6$H$_5$CH=CHCOCH=CHC$_6$H$_5$],
bis(acetonitrile)palladium (II) chloride [Pd(CH$_3$CN)$_2$Cl$_2$],
benzyl[bis(triphenylphosphine)]palladium(II) chloride [C$_6$H$_5$CH$_2$Pd(PPh$_3$)$_2$Cl].

The palladium complex can also be prepared in situ, according to the known techniques, adding to the reaction mixture, a palladium salt and the appropriate ligand, dissolved in the reaction solvent selected from DMSO and DMF. Palladium salts which can be conveniently used are for example the chloride, bromide, iodide, nitrate, acetate, trifluoroacetate and acetylacetonate; ligands which can be conveniently used are, for example, trialkyl and triaryl phosphines and, in particular, triphenylphosphine, o-tolylphosphine, m-tolylphosphine and p-tolylphosphine.

The complexes palladium(II) bis(triphenylphosphine) acetate and palladium(II) bis(triphenylphosphine) chloride, for example, can be formed in the reaction environment starting from commercial precursors such as triphenylphosphine and palladium (II) acetate or chloride, respectively.

It is possible to operate, for example, by mixing the two reagents, the palladium salt and ligand, in the anhydrous dimethylsulfoxide or dimethylformamide solvent and adding the solution thus obtained to the benzothiadiazole having formula (A). It is preferable to operate under nitrogen. The mixture is heated to a temperature higher than 110° C. and the stannane having formula (C) in solution of the same anhydrous solvent previously used for preparing the solution containing the Pd salt and ligand, is added, preferably within a time ranging from 5 to 20 minutes. The reaction is continued until it is complete, preferably within a time of less than 1 hour, even more preferably ranging from 10 to 35 minutes.

If a preformed palladium complex is used, the benzothiadiazole having formula (A) is mixed with the palladium complex dissolved in the anhydrous dimethylsulfoxide or dimethylformamide solvent. The mixture is heated to a temperature higher than 110° C. and the stannane having formula (C) in solution of the same anhydrous solvent previously used for preparing the solution containing the Pd complex, is added preferably within a time ranging from 5 to 20 minutes. The reaction is continued until it is complete, preferably within a time of less than 1 hour, even more preferably ranging from 10 to 35 minutes.

In both procedures, at the end of the process, the reaction mixture can be poured in water and a solvent selected, for example, from ethyl acetate, ethyl ether or dichloromethane, preferably ethyl acetate. Two phases form, which are separated: the desired product is recovered from the organic phase by evaporation and can be purified by crystallization.

The amount of palladium used ranges from 0.01 to 0.1 moles per 100 moles of compound having formula (B), and preferably from 0.04 to 0.06 moles per 100 moles of (B). These values are much lower than those described in the prior art, which normally range from 0.5 to 2 moles of palladium per 100 moles of 4,7-dihalogen-2,1,3-benzothiadiazole.

According to the invention, the reaction is carried out at a temperature preferably higher than 120° C., even more preferably higher than 120° C. and lower than or equal to 160° C. A particularly preferred aspect is to effect the process of the present invention at a temperature ranging from 140 to 150° C.

As far as the pressure is concerned, it is possible to operate either at atmospheric pressure or at a pressure higher than atmospheric pressure, and preferably at atmospheric pressure.

The process of the present invention allows compounds having formula (A) to be prepared, which can be used as spectrum convertor materials and which can be conveniently used in solar concentrators, and in particular 4,7-di-2-thienyl-2,1,3-benzothiadiazole, with high reaction rates, in shorter times, using a stoichiometric ratio between the reagents and in the presence of smaller amounts of catalyst without, however, any increase in the formation of by-products.

The following examples are provided for illustrative purposes of the invention claimed herein without however limiting its objectives in any way.

EXAMPLE 1

In DMSO, with the Catalyst Prepared in situ 1.00 g (3.4 mmoles) of 4,7-dibromo-2,1,3-benzo-thiadiazole and 18 ml of a solution in anhydrous DMSO containing palladium acetate and triphenylphosphine in concentrations of $9.44 \times 10^{-5}$ M and $2.36 \times 10^{-4}$ M, respectively, are charged under a nitrogen flow into a 3-necked 50 ml flask, equipped with magnetic stirring, thermometer, cooler and drip funnel. The amount of palladium is therefore $1.7 \times 10^{-5}$ moles, corresponding to 0.05 moles per 100 moles of 4,7-dibromo-2,1,3-benzothiadiazole. The mixture is heated to 145° C. and a solution of 2.54 g (6.8 mmoles) of tri-n-butyl(thien-2-yl)stannane in 7 ml of anhydrous DMSO, are added through the drip funnel over a time of 20 minutes. At the end of the addition, the reaction is continued for a further 15 minutes and then the advance degree is checked by gaschromatographic analysis which indicates that DTB has been formed with a yield of 99%. The reaction mixture is then poured in water and ethyl acetate obtaining two phases: one prevalently organic and the other prevalently aqueous. The former is extracted three times with water to remove the DMSO; the aqueous phases are collected and extracted once or twice with ethyl acetate. The organic phases are collected, dried on anhydrous sodium sulfate (30 minutes under stirring) and filtered. The solvent is then removed in a rotating evaporator. Possible residual traces of DMSO can be removed by maintaining the residue under a nitrogen flow. The residue is recovered in the minimum volume of a 1:4 mixture of ethyl acetate and n-heptane and the resulting solution is filtered on a cake of $SiO_2$. The filtrate is brought to boiling point for a few minutes (causing a partial evaporation of the solvent) and then cooled to 0° C. obtaining 1.01 g of orange crystals of DTB (99% yield).

EXAMPLE 2

In DMSO, with a Preformed Catalyst

The same procedure is adopted as described in Example 1, charging into the 50 ml flask, in addition to 1.00 g of 4,7-dibromo-2,1,3-benzothiadiazole, 18 ml of a solution in anhydrous DMSO containing $Pd(PPh_3)_2Cl_2$ in concentration $9.44 \times 10^{-5}$ M. The amount of palladium is therefore $1.7 \times 10^{-5}$ moles, corresponding to 0.05 moles per 100 moles of 4,7-dibromo-2,1,3-benzothiadiazole. The same procedure is adopted as in Example 1 obtaining the same yield of pure DTB (99%).

EXAMPLE 3

In DMF, with the Catalyst Prepared in situ

The same procedure is adopted as described in Example 1, charging into the 50 ml flask, in addition to 1.00 g of 4,7-dibromo-2,1,3-benzothiadiazole, 18 ml of a solution of anhydrous DMF containing palladium (II) acetate and triphenylphosphine in concentration $1.89 \times 10^{-1}$ M and $4.72 \times 10^{-1}$ M, respectively. The amount of palladium is therefore $3.4 \times 10^{-6}$ moles, corresponding to 0.1 moles per 100 moles of 4,7-dibromo-2,1,3-benzothiadiazole. The mixture is heated to 145° C. and a solution of 2.54 g (6.8 mmoles) of tri-n-butyl(thien-2-yl)stannane in 7 ml of anhydrous DMF, are added through the drip funnel over a time of 20 minutes. At the end of the addition, the reaction is continued for a further 15 minutes and then the advance degree is checked by gaschromatographic analysis which indicates that DTB has been formed with a yield of 99%. The reaction mixture is then poured in water and ethyl acetate obtaining two phases: one prevalently organic and the other prevalently aqueous. The former is extracted three times with water to remove the DMF; the aqueous phases are collected and extracted once or twice with ethyl acetate. The organic phases are collected, dried on anhydrous sodium sulfate (30 minutes under stirring) and filtered. The solvent is then removed in a rotating evaporator. Possible residual traces of DMF can be removed by maintaining the residue under a nitrogen flow. The residue is recovered in the minimum volume of a 1:4 mixture of ethyl acetate and n-heptane and the resulting solution is filtered on a cake of $SiO_2$. The filtrate is brought to boiling point for a few minutes (causing a partial evaporation of the solvent) and then cooled to 0° C. obtaining 0.97 g of orange crystals of DTB (95% yield)

EXAMPLE 4

In DMF, with a Preformed Catalyst

The same procedure is adopted as described in Example 3, but charging into the 50 ml flask, in addition to 1.00 g of 4,7-dibromo-2,1,3-benzothiadiazole, 18 ml of a solution in anhydrous DMF containing $Pd(PPh_3)_2Cl_2$ in concentration $1.89 \times 10^{-4}$ M. The amount of palladium is therefore $3.4 \times 10^{-6}$ moles, corresponding to 0.1 moles per 100 moles of 4,7-dibromo-2,1,3-benzothiadiazole. The same procedure is adopted as in Example 3 obtaining the same yield of DTB (95%).

The invention claimed is:

1. A process for the preparation of compounds having general formula (A):

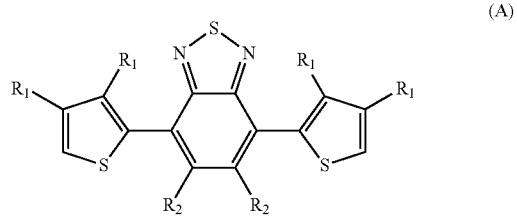

wherein:
the two thienyl groups —$C_4HS(R_1)_2$ are the same,
each $R_1$ of the thienyl group is independently selected from H, linear or branched alkyl, cycloalkyl, aryl, alkyl-aryl, alkoxyl, or substituted alkoxyl,
each $R_2$ is independently selected from H, linear or branched alkyl, cycloalkyl, aryl, alkyl-aryl, alkoxyl, or substituted alkoxyl, or
the adjacent $R_1$ groups of the thienyl group and/or adjacent $R_2$ groups, are bound to each other and, together with the carbon atoms to which they are bound, form a cycle or a polycyclic system, aliphatic or aromatic, or containing one or more heteroatoms, wherein said process comprises reacting, in the presence of a Pd-containing catalyst, at a temperature higher than 120° C. and lower than or equal to 160° C. and in the presence of a solvent selected from dimethylsulfoxide (DMSO) and dimethylformamide (DMF), a compound having formula (B), wherein:

X is a halogen selected from Cl, Br and I, each $R_2$ is independently selected from H, linear or branched alkyl, cycloalkyl, aryl, alkyl-aryl, alkoxyl, or substituted alkoxyl, or the adjacent $R_2$ groups are bound to each other and, together with the carbon atoms to which they are bound, form a cycle or a polycyclic system, aliphatic or aromatic, or containing one or more heteroatoms,

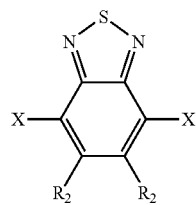

(B)

with a compound having formula (c)

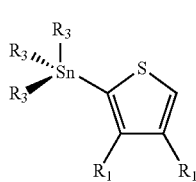

(C)

wherein: each $R_1$ is independently H, linear or branched alkyl, cycloalkyl, aryl, alkyl-aryl, alkoxyl, or substituted alkoxyl, or the $R_1$ adjacent groups are bound to each other and, together with the carbon atoms to which they are bound, form a cycle or a polycyclic system, aliphatic or aromatic, or containing one or more heteroatoms, and $R_3$ is an alkyl containing from 1 to 6 carbon atoms;

wherein:

the molar ratio between the compound having formula (C) and the compound having formula (B) is equal to 2;

the palladium is used in an amount ranging from 0.01 to 0.1 moles per 100 moles of compound having formula (B); and said process is carried out within a time ranging from 10 to 35 minutes.

2. The process according to claim 1, wherein, when at least one of the $R_1$ groups and/or at least one of the groups $R_2$ is linear or branched alkyl, cycloalkyl, aryl, alkyl-aryl, alkoxyl, or substituted alkoxyl, said group contains from 1 to 10 carbon atoms.

3. The process according to claim 1, wherein all the $R_1$ and $R_2$ groups are H.

4. The process according to claim 1, wherein the adjacent $R_1$ groups of the thienyl group and/or the adjacent $R_2$ groups, together with the carbon atoms to which they are bound, form a cycle or a polycyclic system, aliphatic or aromatic, or containing one or more heteroatoms, containing from 3 to 14 carbon atoms.

5. The process according to claim 1, wherein $R_3$ is an alkyl containing from 1 to 4 carbon atoms.

6. The process according to claim 1 for preparing the compound having formula (A) wherein all the $R_1$ and $R_2$ groups are H, which comprises reacting the compound having formula (B) wherein X is a halogen selected from Cl, Br and I and the $R_2$ groups are H, with the compound having formula (C) wherein the $R_1$ groups are H and $R_3$ is alkyl containing from 1 to 6 carbon atoms.

7. The process according to claim 1 for preparing the compound having formula (A) wherein all the $R_1$ and $R_2$ groups are H, which comprises reacting the compound having formula (B) wherein X is Br and the $R_2$ groups are H, with the compound having formula (C) wherein the $R_1$ groups are hydrogen and $R_3$ is n-butyl.

8. The process according to claim 1, wherein the palladium is in oxidation state (0) or (II).

9. The process according to claim 8, wherein the palladium is in the form of a complex.

10. The process according to claim 9, wherein the palladium complex is selected from the group consisting of:
bis(triphenylphosphine)palladium (II) chloride [Pd(PPh$_3$)$_2$Cl$_2$]
bis(triphenylphosphine)palladium (II) acetate [Pd(PPh$_3$)$_2$(OAc)$_2$],
tetrakis(triphenylphosphine)palladium (0) [Pd(PPh$_3$)$_4$],
bis(dibenzylideneacetone)palladium (0) [Pd(dba)$_2$; dba: C$_6$H$_5$CH═CHCOCH═CHC$_6$H$_5$],
bis(acetonitrile)palladium (II) chloride, [Pd(Ch$_3$CN)$_2$Cl$_2$], and
benzyl[bis(triphenylphosphine)]palladium (II) chloride [C$_6$H$_5$CH$_2$Pd(PPh$_3$)$_2$Cl].

11. The process according to claim 1, wherein the palladium is in an amount ranging from 0.04 to 0.06 moles per 100 moles of compound having formula (B).

12. The process according to claim 9, wherein the palladium complex is formed in the same reaction environment.

13. The process according to claim 1, wherein the temperature ranges from 140 to 150° C.

14. The process according to claim 1, wherein the solvent is dimethylsulfoxide (DMSO).

* * * * *